(12) United States Patent
Berckmans et al.

(10) Patent No.: US 11,311,221 B2
(45) Date of Patent: Apr. 26, 2022

(54) METHOD AND DEVICE FOR ACCURATE REAL-TIME DETECTION OF DROWSINESS IN OPERATORS USING PHYSIOLOGICAL RESPONSES

(71) Applicant: BioRICS N.V., Heverlee (BE)

(72) Inventors: Daniel Berckmans, Kessel-Lo (BE); Jean-Marie Aerts, Haasrode (BE); Vasileios Exadaktylos, Salonika (GR); Joachim Taelman, Herent (BE)

(73) Assignee: BioRICS N.V., Heverlee (BE)

( * ) Notice: Subject to any disclaimer, the term of this patent is extended or adjusted under 35 U.S.C. 154(b) by 1170 days.

(21) Appl. No.: 14/451,987

(22) Filed: Aug. 5, 2014

(65) Prior Publication Data

US 2015/0038855 A1 Feb. 5, 2015

(30) Foreign Application Priority Data

Aug. 5, 2013 (GB) ..................................... 1313986

(51) Int. Cl.
*A61B 5/18* (2006.01)
*G08B 21/06* (2006.01)
(Continued)

(52) U.S. Cl.
CPC ............ *A61B 5/18* (2013.01); *A61B 5/02055* (2013.01); *A61B 5/7275* (2013.01); *A61B 5/746* (2013.01);
(Continued)

(58) Field of Classification Search
None
See application file for complete search history.

(56) References Cited

U.S. PATENT DOCUMENTS 6,265,978 B1 7/2001 Atlas
6,337,629 B1 * 1/2002 Bader .................. A61B 5/0205
340/575

(Continued)

FOREIGN PATENT DOCUMENTS

GB 2375645 A 11/2002
GB 2486943 A 7/2012
(Continued)

OTHER PUBLICATIONS

Legge et al. Fatigue is significant in vasovagal syncope and is associated with autonomic symptoms; Europace (2008) 10, 1095-1101.*

(Continued)

*Primary Examiner* — Jay B Shah
(74) *Attorney, Agent, or Firm* — Browdy and Neimark, P.L.L.C.

(57) ABSTRACT

A method and device for detection of drowsiness of a person, based on a relationship between distal temperature and heart rate and on a balance between body heat loss and body heat production, wherein the distal temperature in a predetermined distal region of the person is monitored as a measure for body heat loss, and the heart rate of the person is monitored as a measure for body heat production, wherein drowsiness in the immediate future is concluded when a change of distal temperature passes a first threshold and, subsequently, a change of the heart rate passes a second threshold or, subsequently, the change of the distal temperature is larger than the change of the heart rate.

6 Claims, 8 Drawing Sheets

(51) Int. Cl.
*G16H 50/20* (2018.01)
*G16H 40/63* (2018.01)
*A61B 5/0205* (2006.01)
*A61B 5/00* (2006.01)

(52) U.S. Cl.
CPC ............. *G08B 21/06* (2013.01); *G16H 40/63* (2018.01); *G16H 50/20* (2018.01)

(56) References Cited

U.S. PATENT DOCUMENTS

| | | | | |
|---|---|---|---|---|
| 6,895,275 | B2* | 5/2005 | Markowitz | A61N 1/36521 |
| | | | | 607/18 |
| 2007/0173727 | A1* | 7/2007 | Naghavi | A61B 5/01 |
| | | | | 600/483 |
| 2010/0234747 | A1* | 9/2010 | Hatakeyama | A61B 5/02405 |
| | | | | 600/509 |

FOREIGN PATENT DOCUMENTS

| | | |
|---|---|---|
| GB | 2491984 A | 12/2012 |
| JP | 2011123653 A | 6/2011 |

OTHER PUBLICATIONS

Raymann et al. Skin temperature and sleep-onset latency: Changes with age and insomnia; Physiology & Behavior 90 (2007) 257-266.*

J.F. Pagel, Excessive Daytime Sleepiness; American Family Physician; vol. 79, No. 5 ♦ Mar. 1, 2009 (Year: 2009).*

Ashley Craig et al., "A controlled investigation into the psychological determinants of fatigue", Biological Psychology 72 (2006) 78-87.

* cited by examiner

METHOD AND DEVICE FOR ACCURATE REAL-TIME DETECTION OF DROWSINESS IN OPERATORS USING PHYSIOLOGICAL RESPONSES

FIELD

The present invention concerns a method and device for detection of drowsiness of a person, such as a machine operator, pilot, driver or conductor, wherein a distal temperature in a predetermined distal region of the person and a heart rate of the person are measured and monitored. According to the present invention drowsiness includes micro sleep events (MSE) and falling asleep.

BACKGROUND

Drowsiness and falling asleep of operators are identified as reasons for many fatalities. For example, in the early 1990s researchers using epidemiologic data began investigating sleepiness and sleep deprivation as causes of accidents. Falling asleep while driving associated with sleep restriction and nocturnal driving has been incriminated in 20% of traffic accidents (Philip and Sagaspe, 2011). Therefore, it is important that drowsiness while operating means of transport or other processes can be detected in an early stage in order to prevent accidents.

It is known that sleep regulatory and thermoregulatory systems in homeotherms are closely interrelated (Krauchi, 2007). Both are driven, independently, by two interacting physiological principles, homeostasis and circadian regulation.

The human body consists of two thermophysiological compartments, the heat producing, homeothermic core, and the heat loss regulating, poikilothermic shell (Mount, 1979). All peripheral tissues such as fat, skin, and in particular skeletal muscles of the legs and the arms can contribute substantially to the size of the shell, provided that peripheral flow is low. Therefore, rates of blood flow through muscles and skin are the main determinants of the shell size variability and hence of peripheral insulation. The distal skin regions, in particular fingers and toes, are the main thermoeffectors of the body to lose body heat. Therefore, the distal skin temperatures provide a good measure of the shell size (Krauchi and de Boer, 2010).

Thermoregulatory distal skin blood flow is regulated by the autonomic nervous system via constriction or dilatation of arteriovenous anastomoses (AVA's). These are shunts between arterioles and venules, exclusively found in distal skin regions, e.g. fingers and toes. When they are open warm blood flows rapidly and directly from arterioles to the dermal venous plexus enabling an efficient heat exchange from the core to the distal skin. The distal to proximal skin temperature gradient (DPG), i.e. the difference between the distal and proximal skin temperature, provides a selective measure of distal skin blood flow, and hence body heat loss via the extremities. Heart rate (HR) can be seen as an indirect measure of intrasubject variation of heat production. So, measuring distal and proximal skin temperature and heart rate allows estimating indirectly (changes in) heat loss and heat production.

Typically, when falling asleep, heat production is first lowered by a decrease in the heart rate, followed by an increase in distal temperatures and an increase in heat loss, resulting in a decrease in core body temperature (CBT). Before falling asleep, people can experience feelings of light to heavy drowsiness and even micro sleep events (MSE), which are brief unintended episodes with loss of attention and which can be potentially dangerous, especially when operating processes such as driving a vehicle or a train, flying an airplane, navigating a ship, air traffic control, etc.

Current systems for detection of drowsiness are based on, e.g., changes of heart rate, temperature changes of breath, skin or eyes, movement of head and eyelids or movement of the steering wheel. However, the accuracy of the present systems is rather low such that operators ignore warning signals which often occur much too early. A warning signal indicating that drowsiness will occur within 30 to 60 minutes or more, will in most circumstances be ignored and hence will be ineffective.

Patents GB-2375645-A and GB-2491984-A both describe a system and method for detection of drowsiness in which instantaneous absolute values for body temperature and/or heart rate are compared with a threshold consisting of a steady state reference value for each individual in sleeping or drowsy state. Consequently, these systems need thorough calibration and determination of specific reference threshold values for each individual.

SUMMARY

The invention aims to remedy the above mentioned disadvantages of existing detection systems. Therefore, for developing monitor systems for drowsiness detection, distal temperatures and heart rate should be monitored in real-time and the relationship between distal temperatures and heart rate is a key feature in the determination and prediction of the level of drowsiness.

The aim of the present invention is to provide a method and device allowing reliable, accurate and real-time detection of drowsiness in operators. Hence, the invention aims to offer a method and device to predict if future drowsiness or MSEs will occur and to predict when drowsiness or MSEs will occur.

The above mentioned objects are realised by the method and device having the specific features set out in the appended claims. Specific features for preferred embodiments of the invention are set out in the dependent claims.

Practically, the method and device, according to the invention, is based on a relationship between the distal temperature and the heart rate, wherein the distal temperature is a measure for body heat loss and the heart rate is a measure for body heat production. A change of the distal temperature is compared with a first threshold and, after passing this first threshold, a change of the heart rate is compared with a second threshold or with the change of the distal temperature, wherein drowsiness in the immediate future is concluded when the change of distal temperature passes the first threshold and, subsequently, the change of the heart rate passes the second threshold or, subsequently, the change of the distal temperature is larger than the change of the heart rate.

According to the invention the immediate future refers to a period of less than 60 minutes, preferably less than 30 minutes, in which drowsiness will occur. Advantageously, the immediate future corresponds to a period of approximately 10 to 15 minutes.

Other particularities and advantages of the invention will become clear from the following description and accompanying drawings of practical embodiments of the method and device of the invention; the description and drawings are

DETAILED DESCRIPTION

The invention generally concerns a method and device for detection of drowsiness of a person wherein drowsiness of the person is determined after evaluating a change in the balance between body heat loss and body heat production. The method is based on a relationship between distal temperature and heart rate, which reflects the balance between body heat loss and body heat production. According to the method of the invention, a distal temperature (Td) in a predetermined distal region of the person is measured and monitored as a measure for body heat loss, and a heart rate (HR) of the person is measured and monitored as a measure for body heat production.

The method is based on dynamics of measured thermoregulatory signals, e.g. changes of distal temperature and heart rate. This has the advantage that it allows detecting thermoregulatory changes that precedes drowsiness, e.g. up to 45 minutes for some subjects, before the steady state values of body temperature and/or heart rate start dropping.

In order to predict and monitor the drowsiness in practice, an apparatus is needed consisting of a sensing unit, a computing unit, a warning unit and/or an output unit. The sensing unit includes a temperature sensor and a heart rate sensor. It measures the heart rate (HR) and the distal temperature (Td). Both measured bio-signals are processed in real-time in the computing unit. The computing unit communicates with a warning and/or output unit, which generates warnings for the operator. The apparatus can be made mobile where the operator wears the sensors and the computing power (e.g. smart phone) on the body, or the measuring hardware and computing power can be integrated in the operator's environment (e.g. via the roof of a car, the seat, the seat belt or the head support).

Figure 1:
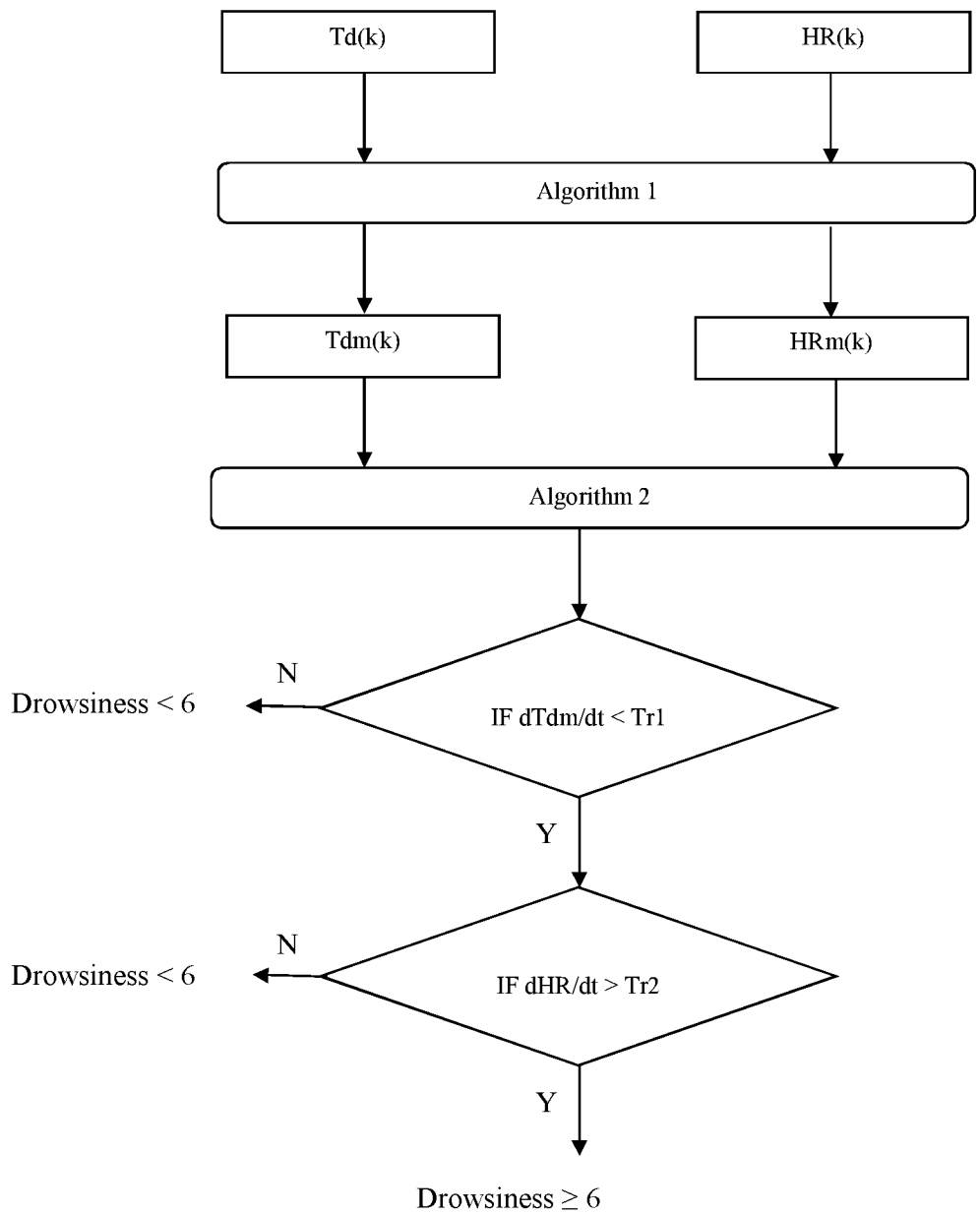
FIG. 1 is a flow chart of the method according to a first embodiment of the invention.
Figure 2:
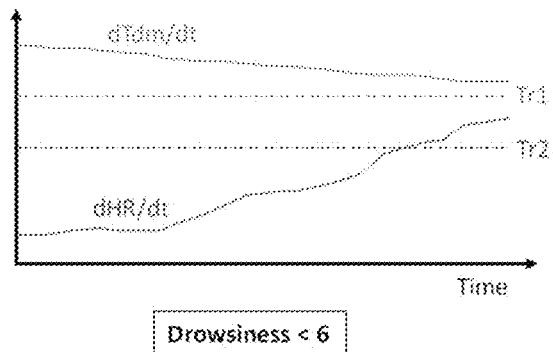
FIG. 2 is a graph, which schematically represents the slopes (dHRm/dt and dTdm/dt) of the overall trends of the mean values of the distal temperature (Tdm) and the heart rate (HRm) according to the first embodiment of the invention, wherein dTdm/dt does not cross a first threshold (Tr1) and dHR/dt does not cross a second threshold (Tr2) and thus the subject person is evaluated as not drowsy.
Figure 3:
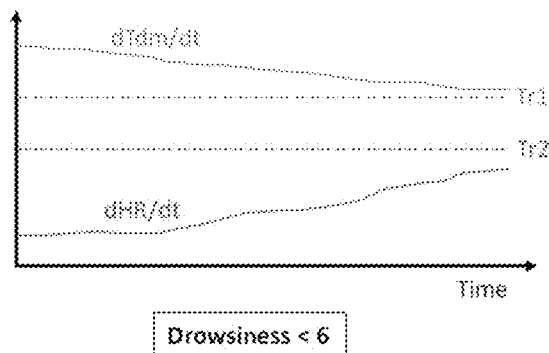
FIG. 3 is a graph as in FIG. 2, wherein dTdm/dt does not cross Tr1 and dHR/dt does cross Tr2 and thus the subject person is evaluated as not drowsy.
Figure 4:
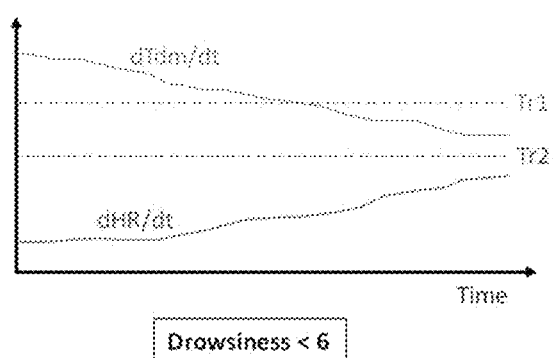
FIG. 4 is a graph as in FIG. 2, wherein dTdm/dt does cross Tr1 and dHR/dt does not cross Tr2 and thus the subject person is evaluated as not drowsy.
Figure 5:
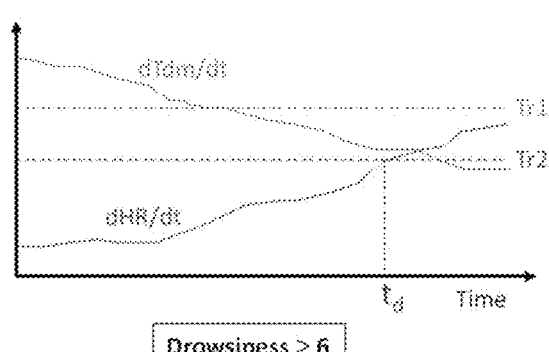
FIG. 5 is a graph as in FIG. 2, wherein dTdm/dt does cross Tr1 and subsequently dHR/dt does cross Tr2 and thus the subject person is evaluated as drowsy.

A first embodiment of a method according to the invention is schematically shown in the flow chart of FIG. 1.

The heart rate (HR) of a person and the distal temperature (Td) at an ear of the person are measured and monitored.

A first algorithm (Algorithm 1) is used for estimation of slow varying trends in the distal temperature (Td) and the heart rate (HR). The algorithm (Algorithm 1) calculates global trends in the real-time measured distal temperature (Td) and heart rate (HR) time series by calculating progressing overall mean values of distal temperature (Tdm) and heart rate (HRm). The progressing overall mean value at a time instant is the mean calculated at said time instant starting from the first measured value of a time series. It is a recursively estimated mean of a time series by calculating each new time instant the average of all values from the start of the time series until the last measured data point.

In order to estimate the relative balance between heat production, which is related to the heart rate (HR) and heat losses, which is related to the distal temperature (Td), changes in the distal temperature (dTd/dt) and changes in the heart rate (dHR/dt) are monitored using a second algorithm (Algorithm 2) for the estimation of slopes in slow varying trends of the distal temperature (Td) and the heart rate (HR). By using a dynamic linear regression approach, the second algorithm (Algorithm 2) quantifies at each time instance the slopes of slow trends of progressing overall mean values of the distal temperature (Tdm) and the heart rate (HRm) calculated by means of the first algorithm (Algorithm 1).

The slopes (dHRm/dt, dTdm/dt) of overall trends of mean values of the distal temperature (Tdm) and the heart rate (HRm) are schematically represented in FIGS. 2 to 5.

When the slope of the trend of the mean value of the distal temperature (dTdm/dt) crosses a predefined first threshold (Tr1), the slope of the trend of the mean value of the heart rate (dHRm/dt) is monitored. When the latter, subsequently, crosses a second threshold (Tr2), the operator is defined to be drowsy, as schematically represented in the graph of FIG.

5. The moment of crossing the second threshold (Tr2) is defined as the moment of onset of drowsiness. In all other cases, schematically represented in FIGS. 2 to 4, the operator is assumed to be not drowsy. Hence, for the scenario when dTdm/dt crosses Tr1, but dHR/dt does not cross Tr2 or when dTdm/dt does not cross Tr1, the operator is assumed not to be drowsy.

In order to test the methodology according to the first embodiment of the invention, an experiment was performed, in which a total of 10 persons (D1 to D10) have been used as test subjects for driving a fully equipped test car. In total 16 datasets were generated. The results are shown in table 1. Depending on the test subject, the drives started in the morning at 10h00, in the afternoon at 15h00, in the evening at 20h00 or at night at 24h00.

For the experiment a test car was used, equipped with the following sensors/sensing systems:

1. faceLAB eye tracking system (60 fps) for measuring of eye movements, head position and rotation, eyelid aperture and pupil size;
2. webcam for registration of driving behaviour (30 fps);
3. car variables measured via the can bus of the test car: longitudinal velocity (m/s); longitudinal acceleration (m/s$^2$); lateral velocity (m/s); lateral acceleration (m/s$^2$); throttle pedal position (%); brake pedal force (N); steering torque (ft-lbs); steering wheel angle (deg); steering wheel angle rate (deg/s).
4. physiological variables: heart rate (HR): sampling rate: 256 Hz, derived from ECG measured wirelessly via chest belt (resolution: 1 bpm); respiration rate: sampling rate: 32 Hz, measured via deformation of chest belt (resolution: 0.01%; range: 0-75%); activity: sampling rate: 128 Hz, measured via accelerometer (resolution: 3 mg; range: +/−6 g); skin temperature: sampling rate: 32 Hz (resolution: 0.1° C.); ear temperature (Td): idem as skin temperature; body temperature (armpit): idem as skin temperature.

TABLE 1

Experimental results of prediction performance of the method of the first embodiment of the invention using distal ear temperature (Td) and heart rate (HR) as measured bio-responses; 11 out of 14 datasets have correctly been classified.

| Test subject Driver code | Drowsiness level ≥6* according to scoring co-driver | Drowsiness level ≥6* according to the method of the first embodiment | Correct prediction | Time difference between predicted and actual onset of drowsiness (min) |
|---|---|---|---|---|
| D1 | No | No | ✓ | — |
| D2 | Yes | Yes | ✓ | −5 |
| D3 | No | No | ✓ | — |
| D4-3 | Yes | Yes | ✓ | 0 |
| D5-1 | No | No | ✓ | — |
| D5-2 | Yes | Yes | ✓ | +10 |
| D6-1 | No | No | ✓ | — |
| D6-2 | No | No | ✓ | — |
| D7 | Yes | No | x | — |
| D8-1 | No | No | ✓ | — |
| D8-2 | Yes | Yes | ✓ | −15 |
| D9-1 | Yes | Yes | ✓ | +25 |
| D9-2 | Yes | No | x | — |
| D10 | No | Yes | x | — |

*The drowsiness level of the driver was scored on a scale from 1, not drowsy at all, to 9, falling asleep; the driver was assumed to be drowsy from a score of 6 on.

A single driving experiment consisted of a four to five hours drive performed by the test subject and an accompanying co-driver. All test subjects followed comparable routes, consisting of a mix of different roads, i.e. highway, express roads and streets. During every drive two persons were present in the car, namely, the test subject as driver and the co-driver who checked continuously the proper functioning of the measuring equipment and monitored the status of the test driver.

Before following the programmed route, each driver made a short drive with the test car (approximately 15 minutes) to get himself acquainted to the car.

The drowsiness level of the test subject, i.e., the driver, was scored by the driver as well as by the co-driver on a scale from 1, corresponding to not drowsy at all, to 9, corresponding to falling asleep. In the results shown in table 1, signals sampled at 1 Hz were used and the driver was assumed to be drowsy from a score of 6 on.

A second embodiment of a method according to the invention uses the relation between the distal temperature (Td) and heart rate (HR) by calculating the difference between measured signals of distal temperature (Td) and heart rate (HR) in order to predict the onset of MSE or drowsiness.

Figure 6:
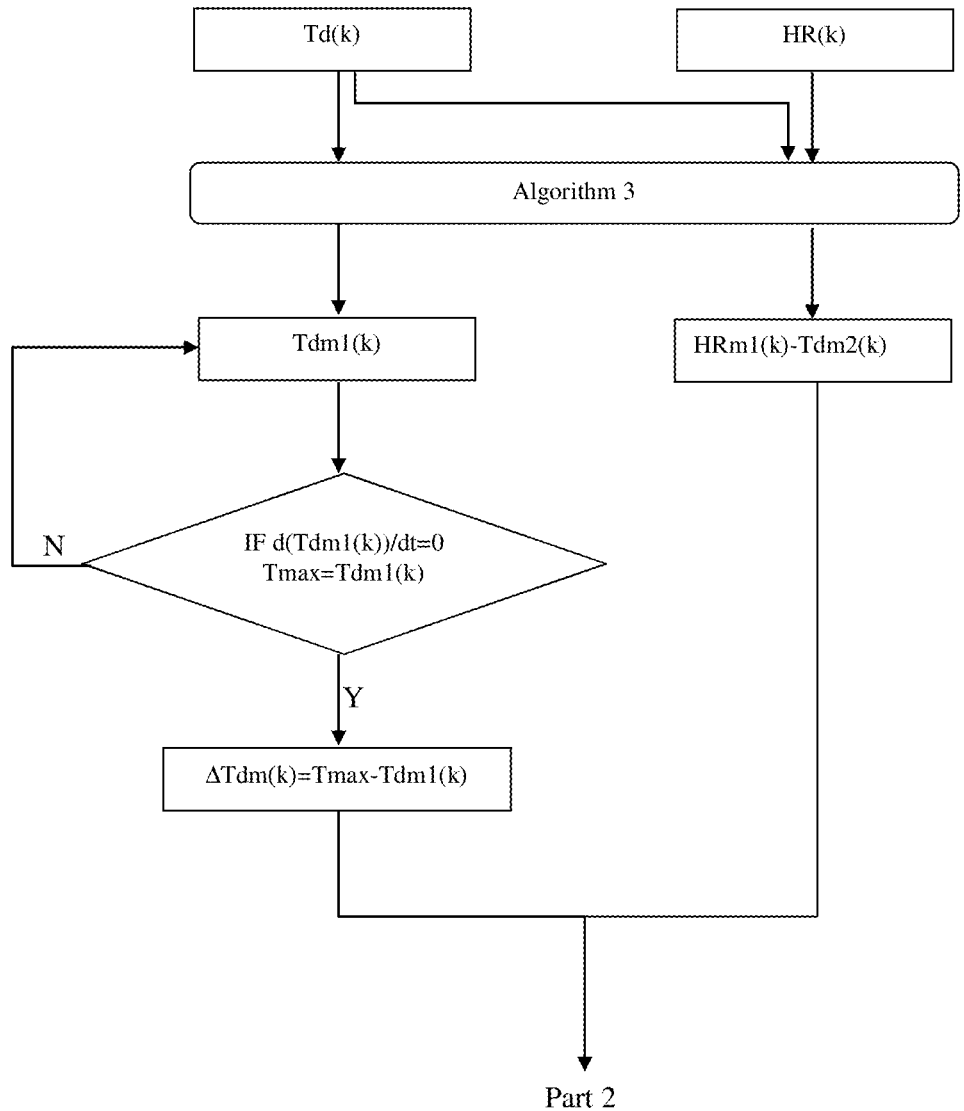
FIGS. 6 and 7 are a flow chart of the method according to a second embodiment of the invention.
Figure 7:
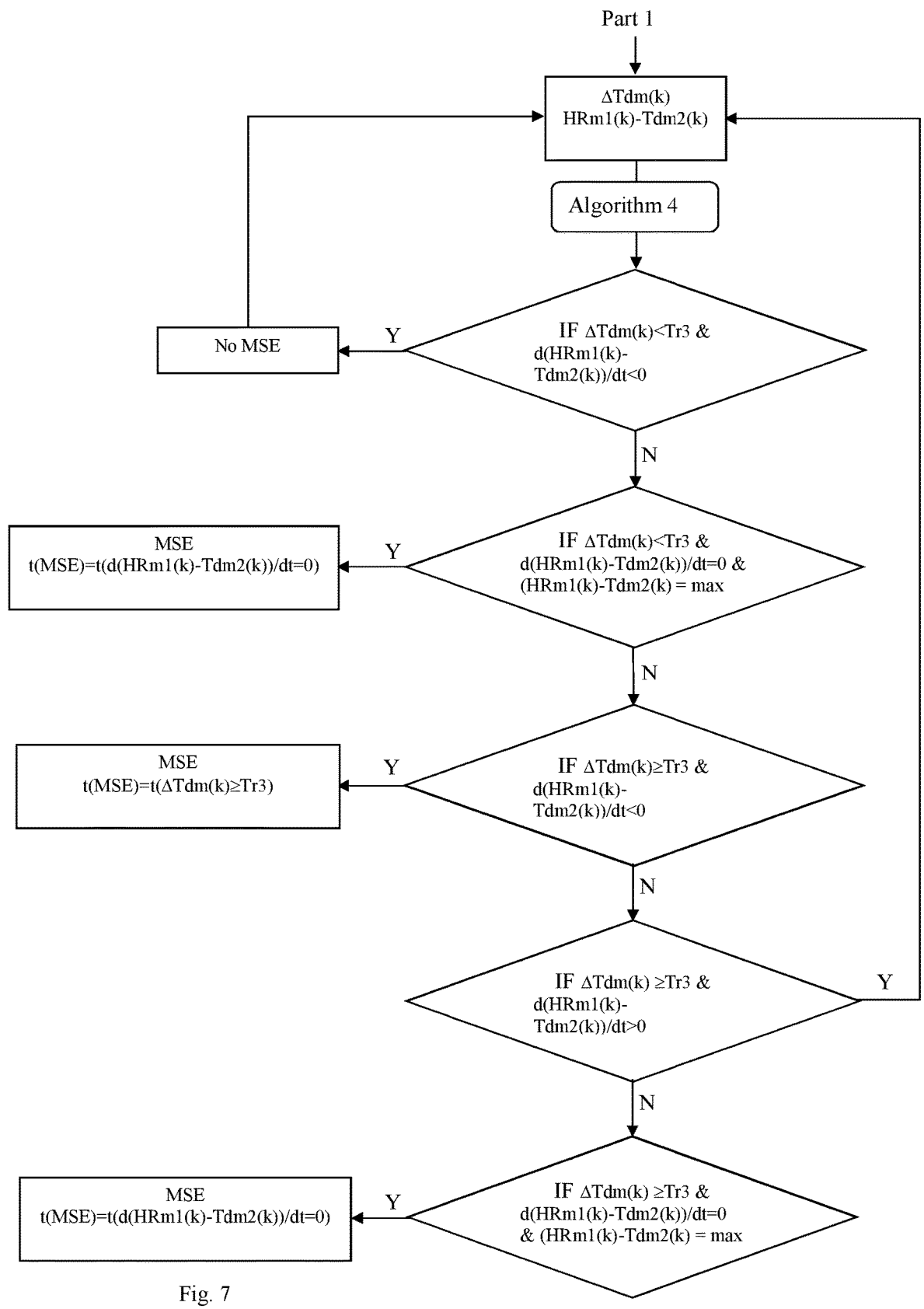
Figure 8:
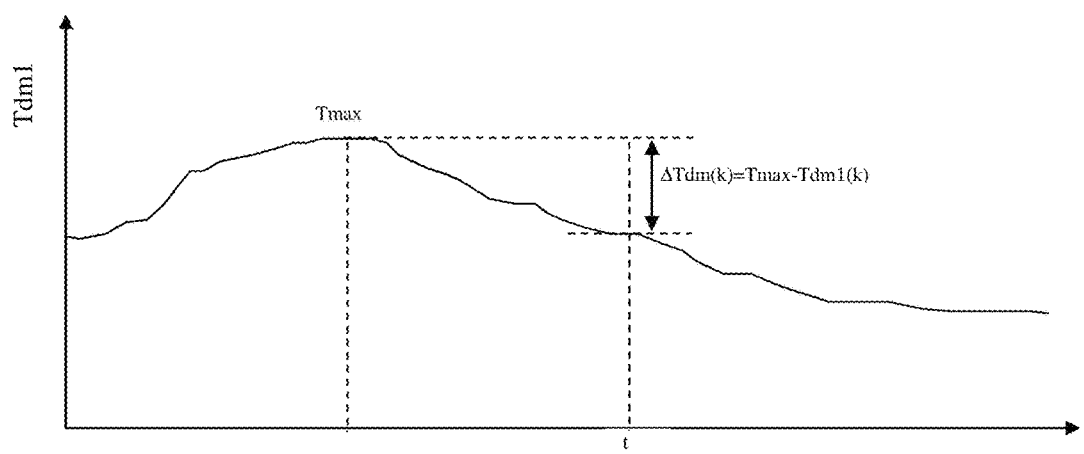
FIG. 8 is a graphical representation of the working of the method of FIGS. 6 and 7.

The method is schematically represented in the flow charts of FIGS. 6 and 7 and further illustrated in the graphical representations of FIGS. 8 to 13.

First, a moving average for the distal temperature (Tdm1) as well as a progressing overall mean for the distal temperature (Tdm2) and the heart rate (HRm) are quantified by use of a first algorithm (Agorithm 3). Next, when the Tdm1 signal reaches a maximum value (Tmax), all next values of Tdm1 are compared with this maximum value (ΔTdm(k) =Tmax−Tdm1(k)).

In parallel, the calculated trends for distal temperature (Tdm2) and heart rate (HRm) are fed into a second algorithm (Algorithm 4) to calculate the slope of HRm-Tdm2.

Next, the calculated value of ΔTdm(k) is compared with a threshold value Tr3 and the slope of HRm-Tdm2 is quantified by use of a second algorithm (Algorithm 4).

Several scenarios can occur that can be linked to the drowsiness state of the operator.

Figure 9:
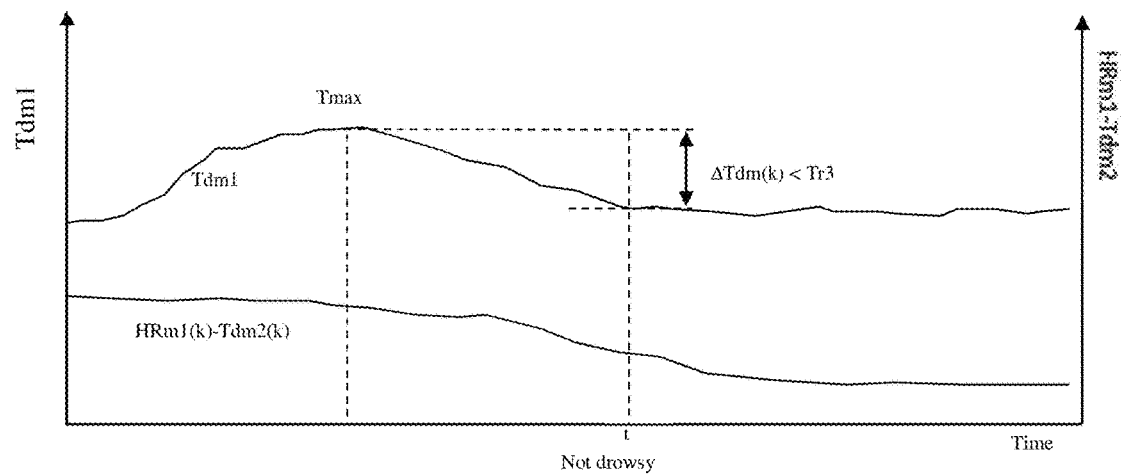
FIG. 9 is a graphical representation of a first scenario according to the second embodiment of the invention, in which the difference between the maximal distal temperature (Tmax) and the actual mean distal temperature (Tdm1(k)) ($\Delta$Tdm(k)=Tmax-Tdm1(k)) is smaller than the first threshold (Tr1) and the slope of HRm1(k)-Tdm2(k) as a function of time is negative and wherein the subject person is evaluated as not drowsy.

In a first scenario, as schematically represented in FIG. 9, ΔTdm(k) is smaller than Tr3, i.e. when the distal temperature Td is quite stable, and the slope of HRm(k)−Tdm2(k) as a function of time is negative, i.e. when the heat production relatively decreases, the operator is considered as being not drowsy.

Figure 10:
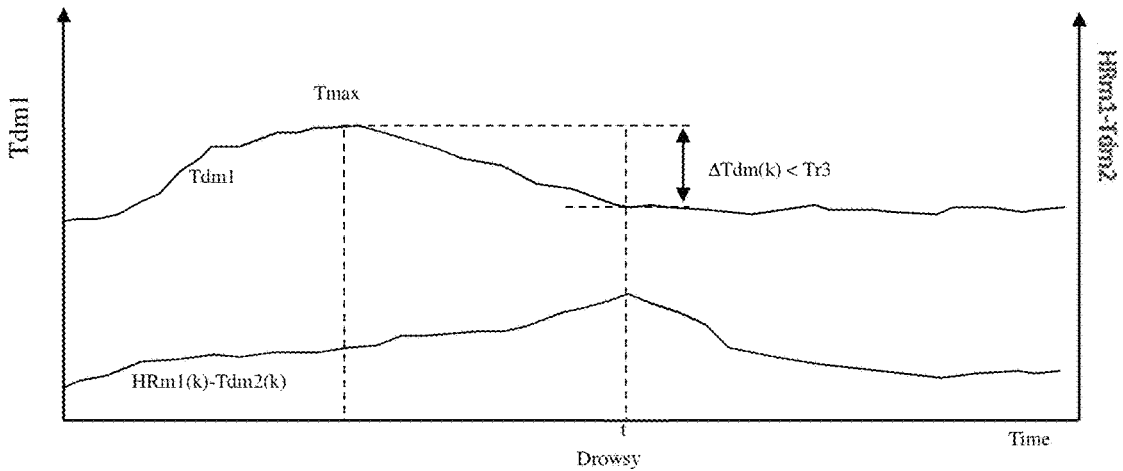
FIG. 10 is a graphical representation of the second embodiment of the invention, in which $\Delta$Tdm(k) is smaller than Tr1 and HRm1(k)-Tdm2(k) as a function of time reaches a maximum value and wherein the subject person is evaluated as drowsy.

In a second scenario, as schematically represented in FIG. 10, ΔTdm(k) is smaller than Tr3 and the slope of HRm(k)−Tdm2(k) as a function of time is zero when HRm(k)−Tdm2 (k) reaches a maximum value, i.e. after a period of increased heat production the heart rate decreases, the operator is considered as being drowsy. The moment of reaching the maximum HRm(k)−Tdm2(k) is the moment that the operator is considered to be drowsy.

Figure 11:
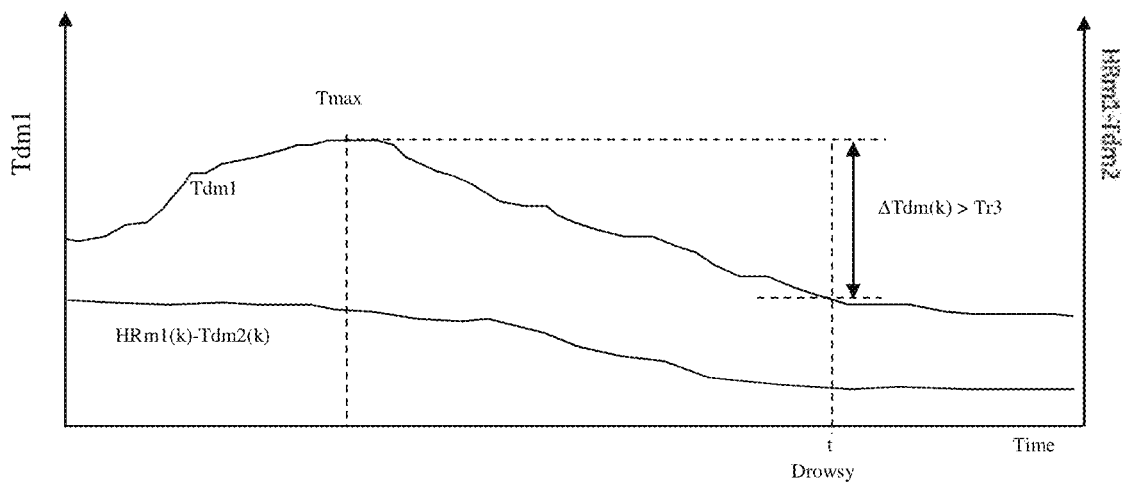
FIG. 11 is a graphical representation of a third scenario, in which $\Delta$Tdm(k) is larger than Tr1 and the slope of HRm1(k)-Tdm2(k) as a function of time is negative and wherein the subject person is evaluated as drowsy.

In a third scenario, as schematically represented in FIG. 11, ΔTdm(k) is larger than Tr3 and the slope of HRm(k)−Tdm2(k) as a function of time is negative, the operator is considered as being drowsy. The moment of crossing the Tr3 value is the moment that the operator is considered to be drowsy.

Figure 12:
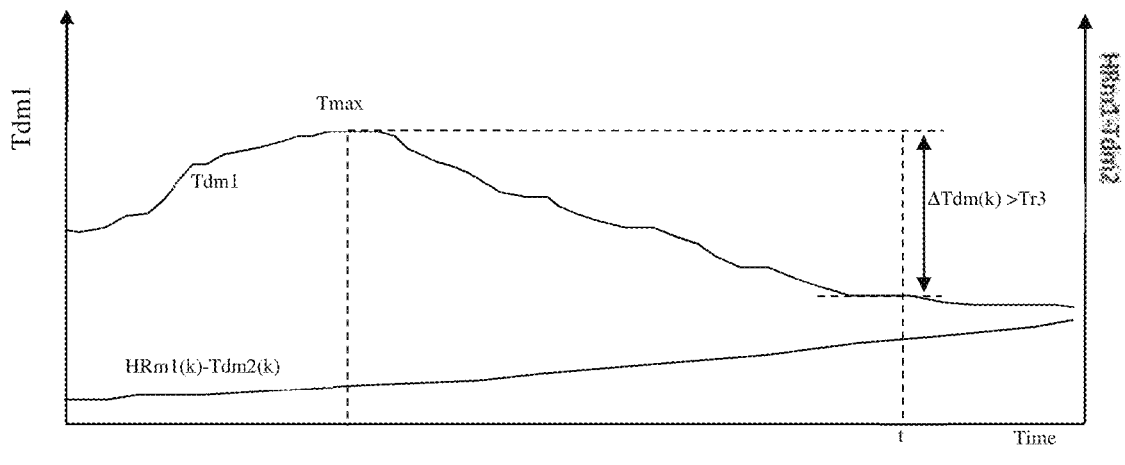
FIG. 12 is a graphical representation of a fourth scenario, in which $\Delta$Tdm(k) is larger than Tr1 and the slope of HRm1(k)-Tdm2(k) as a function of time is positive and wherein the subject person is evaluated as not drowsy.

In a fourth scenario, as schematically represented in FIG. 12, ΔTdm(k) is larger than Tr3, i.e. when there is vasoconstriction in the distal parts and heat loss is lowered, and the slope of HRm(k)−Tdm2(k) as a function of time is positive, i.e. when there is a relative increase in heat production and a decrease in heat loss, the operator is considered as being not drowsy.

Figure 13:
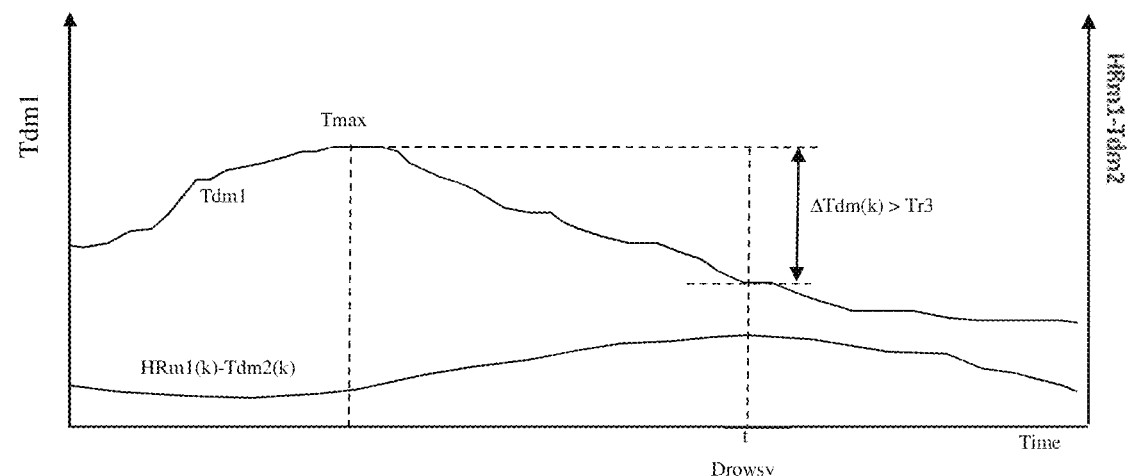
FIG. 13 is a graphical representation of a fifth scenario, in which $\Delta$Tdm(k) is larger than Tr1 and HRm1(k)-Tdm2(k) as a function of time reaches a maximum and wherein the subject person is evaluated as drowsy.

In a fifth scenario, as schematically represented in FIG. 13, ΔTdm(k) is larger than Tr3 and HRm(k)−Tdm2(k) as a function of time reaches a maximum, the operator is considered as being drowsy. The moment of reaching this maximum, after crossing Tr3, is the moment that the operator is considered to be drowsy.

The method according to the second embodiment of the invention was tested on experimental data generated by a driving simulator under controlled conditions. The results are shown in tables 2 and 3.

TABLE 2

Prediction performance of the second embodiment of the method according to the invention on training datasets; 21 out of 24 datasets have been correctly classified.

| Test subject Driver code | MSE predicted | Time difference between predicted and actual onset of MSEs (min) | Correct prediction |
|---|---|---|---|
| D11 | No | — | ✓ |
| D12 | Yes | 30 | ✓ |
| D13 | Yes | −75 | ✓ |
| D14 | Yes | −3 | ✓ |
| D15 | Yes | 15 | ✓ |
| D16 | Yes | −75 | x |
| D17 | Yes | 5 | ✓ |
| D18 | No | — | ✓ |
| D19 | No | — | ✓ |
| D20 | No | — | ✓ |
| D21 | No | — | ✓ |
| D22 | Yes | 5 | ✓ |
| D23 | No | — | ✓ |
| D24 | No | — | ✓ |
| D25 | Yes | 0 | ✓ |
| D26 | Yes | −5 | ✓ |
| D27 | No | — | ✓ |
| D28 | Yes | −35 | x |
| D29 | No | — | ✓ |
| D30 | Yes | −5 | ✓ |
| D31 | Yes | 30 | ✓ |
| D32 | No | — | x |
| D33 | Yes | −15 | ✓ |
| D34 | No | — | ✓ |

More specifically, experiments were designed using in total 63 subjects, including only male subjects, aged 22 to 28 years, right-handed and having a mean driving experience of over 16000 km/year. During the simulator experiments several variables were measured on the car (distance along roadway centreline, total vehicle longitudinal velocity, total vehicle lateral velocity, steering wheel angle, etc.) as well as on the driver. The main physiological variables were: eye movements, eye blink duration, blink frequency, head movements, EEG, galvanic skin response, heart rate, fingertip temperature and armpit temperature. For this analysis 24 test persons (D11 to D34) were used for training the algorithms and 11 test persons (D35 to D45) for validation purposes. The driving tasks were basically divided into three parts: control, drowsiness induction and test.

TABLE 3

Prediction performance of the second embodiment of the method according to the invention on validation datasets; 8 out of 11 datasets have been correctly classified.

| Test subject Driver code | MSE predicted | Time difference between predicted and actual onset of MSEs (min) | Correct prediction |
|---|---|---|---|
| D35 | No | — | ✓ |
| D36 | No | — | ✓ |
| D37 | No | — | ✓ |
| D38 | No | — | ✓ |
| D39 | Yes | 12 | ✓ |
| D40 | Yes | −45 | x |
| D41 | Yes | 0 | ✓ |
| D42 | Yes | 5 | ✓ |
| D43 | No | −10 | x |
| D44 | Yes | 5 | ✓ |
| D45 | Yes | — | x |

During the control part of about 9 km, the subjects drove through tight curves with heavy oncoming traffic, changing visibility (fog banks) and the request to drive as fast as possible. The following drowsiness induction part showed reduced visibility due to fog and a speed limit of 50 km/h throughout the whole length of about 110 km (six identical laps of about 18 km). The test part at the end of the scenario repeated exactly the control part from the beginning.

The driving tasks started at 13h30. During the 2.5 hours long driving task the subject had no access to external stimuli such as a time watch, radio or conversation. In order to get a drowsiness estimation for each subject straight after the trial, the supervisor rated the subjects for six times during the induction part of the trial—each time the subjected started into a new repetition of the induction part. After the trial, the subjects completed the same questionnaires on subjective rating of drowsiness and mood and concentration performance as in the morning and before the driving task, respectively (Altmuller, 2007).

In table 2, results are shown for predicting the onset of the first MSEs on the training datasets. Table 3 shows the results for the validation datasets.

Figure 14:
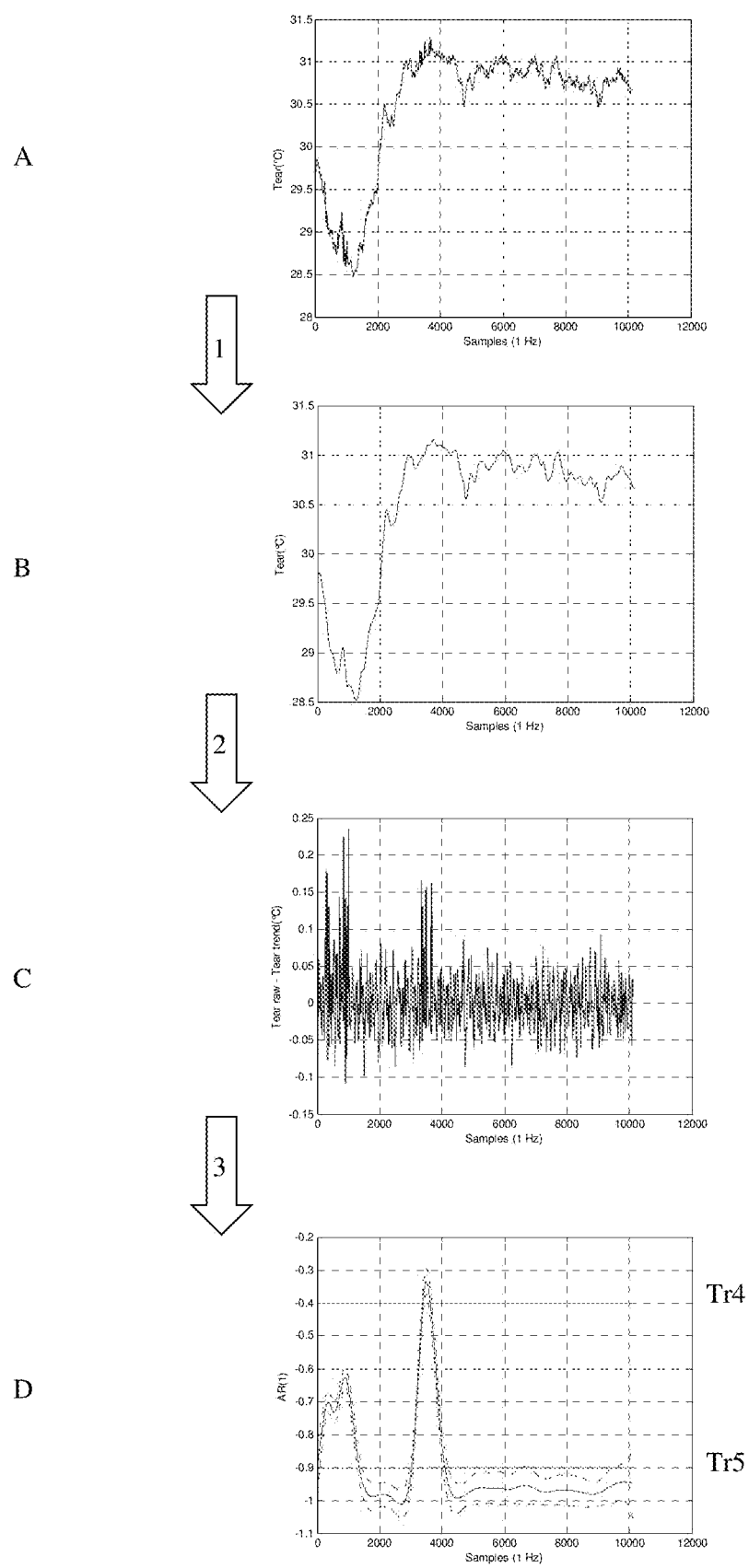
FIG. 14 is a flow chart of the method according to a third embodiment of the invention, including charts of (A) distal temperature (Td), (B) mean values of the distal temperature (Tdm), (C) difference between distal temperature (Td) and mean values of the distal temperature (Tdm), and (D) time-varying parameter of a first order autoregressive model (AR(1)) of the difference between distal temperature (Td) and mean values of the distal temperature (Tdm).

A third embodiment of a method according to the invention differs from the first and second embodiment mainly in the manner that a change of the distal temperature is compared with a first threshold, before comparing a change of the heart rate with a second threshold or with the change of the distal temperature, as schematically presented in FIG. 14 (Algorithm 5).

In this embodiment an alternative methodology early for detection of heavy drowsiness or MSE may be based on only distal temperature measurements (Algorithm 5). More specifically, using an integrated random walk model the overall trend of the distal temperature (Td) is estimated and this trend signal (Tdm) is subtracted from the original measured temperature signal (Td). The integrated random walk model is a time series model that is typically used for estimation of simple trends in time series and for smoothing operations. The resulting difference signal (Td−Tdm) describes mainly the higher frequent behaviour of the distal temperature (Td) and it can be modelled for instance by using a first order time-varying autoregressive analysis, resulting in a time series of AR(1) parameters. The first order time-varying autoregressive model is a model that regresses each value of a time series variable on its previous value. The coefficient or also the parameter describing the linear relationship between each value with its previous value (1st order) can be made function of time itself, resulting in a time-varying autoregressive parameter (AR(1)). The calculated AR(1) parameter values, which are reflecting the dynamics of the thermoregulatory mechanisms, are compared with two threshold values (Tr4, Tr5) in order to determine a state of drowsiness or not.

A schematic overview including graphical representations of the working of the algorithm (Algorithm 5) of the third embodiment is shown in FIG. 14. The different steps are: (1) calculation of slow trend of the original signal, (2) subtracting the trend signal from the original signal and (3) calculating the AR(1) parameters of the difference signal and comparing it with two threshold values (Tr4, Tr5).

When the calculated AR(1) parameter value exceeds a first threshold value (Tr4, Tr5), drowsiness in the near future is expected. For further evaluation of the onset of drowsiness, a change of the heart rate is compared with a second threshold or with the change of the distal temperature, as described for the above first and second embodiments.

TABLE 4

Prediction performance of the third embodiment of the method according to the invention on validation datasets using ear temperature as measured bioresponses; 18 out of 18 datasets have been correctly classified.

| Driver code | Drowsiness ≥7 according to scoring co-driver | Drowsiness ≥7 according to algorithms | Correct prediction |
|---|---|---|---|
| D50 | N | N | ✓ |
| D51 | N | N | ✓ |
| D52 | N | N | ✓ |
| D53 | N | N | ✓ |
| D54 | N | N | ✓ |
| D55 | Y | Y | ✓ |
| D56 | N | N | ✓ |
| D57 | N | N | ✓ |
| D58 | N | N | ✓ |
| D59 | N | N | ✓ |
| D60 | N | N | ✓ |
| D61 | Y | Y | ✓ |
| D62 | N | N | ✓ |
| D63 | N | N | ✓ |
| D64 | N | N | ✓ |
| D65 | N | N | ✓ |
| D66 | N | N | ✓ |
| D67 | N | N | ✓ |

*The drowsiness level of the driver was scored on a scale from 1, not drowsy at all, to 9, falling asleep; the driver was assumed to be drowsy from a score of 6 on.

Naturally, the invention is not restricted to the method and device according to the invention as described above. Thus, besides the distal ear temperature, other distal regions, such as fingers or toes, may be used for measuring the distal temperature. Furthermore, according to the invention the immediate future may also refer to a period of less than 10 minutes. The warning signal may also include an activating signal, which prevents and/or delays drowsiness.

Figure 15:
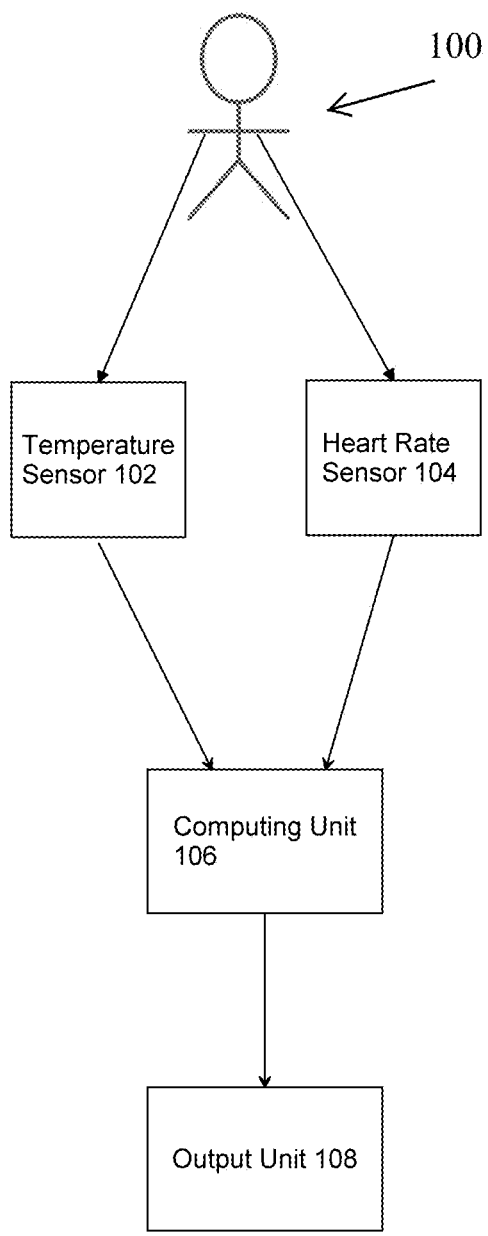
FIG. 15 is a schematic illustration of a device according to the present invention.

An example of a device according to the invention is disclosed, schematically illustrated in FIG. 15, for detection of drowsiness of a person 100, based on a relationship between distal temperature and heart rate. The device includes a temperature sensor 102 for measuring a distal temperature in a predetermined distal region of the person as a measure for body heat loss, a heart rate sensor 104 for measuring a heart rate of the person as a measure for body heat production, a computing unit 106 for monitoring the measured distal temperature and the measured heart rate, and an output unit 108 for generating a drowsiness signal and alerting the person when drowsiness in the immediate future is concluded. According to the invention, the computing unit compares a change of the distal temperature with a first threshold and, after detecting the passing of the first threshold, compares a change of the heart rate with a second threshold or with the change of the distal temperature. The output unit generates the drowsiness signal and alerting the person when the computing unit detects that the change of distal temperature passes the first threshold and, subsequently, detects that the change of the heart rate passes the second threshold and/or the change of the distal temperature is larger than the change of the heart rate.

The computing unit monitors the change in the distal temperature and/or the heart rate, by monitoring the change of averaged values of the measured distal temperature and/or the measured heart rate. The averaged values are a moving average and/or a progressing overall mean.

The computing unit calculates the progressing overall mean distal temperature from the measured distal temperature and calculates the progressing overall mean heart rate from the measured heart rate. The computing unit monitors the change of the progressing overall mean distal temperature and compares it with the first threshold. After the computing unit detects the passing of said first threshold, the computing unit monitors the change of the progressing overall mean heart rate and compares it with the second threshold. The output unit generates the drowsiness signal when the computing unit detects that the change of progressing overall mean distal temperature passes the first threshold and, subsequently, the change of the progressing overall mean heart rate passes the second threshold.

The computing unit detects a maximum in the distal temperature, and monitors the change in the distal temperature after reaching the maximum in the distal temperature, to compare the change with the first threshold corresponding to a maximal change in the distal temperature, and detects when the distal temperature passes the first threshold. The computing unit also monitors a change in the difference between the heart rate and the distal temperature, after detecting the distal temperature passing the first threshold, to compare the change with the second threshold, and detects when the change passes the second threshold. The output unit generates the drowsiness signal to alert the person of the conclusion that drowsiness is impending when the computing unit detects that the distal temperature passes the maximal change in the distal temperature and subsequently detects that the change of the distal temperature is larger than the change of the heart rate or subsequently the change in the distal temperature equals the change in the heart rate.

The output unit generates the drowsiness signal and alerts the person when the computing unit detects that the change in the distal temperature equals the change in the heart rate. The immediate future corresponds to a period of less than 60 minutes, preferably less than 30 minutes, more preferably between 10 minutes and 15 minutes.

REFERENCES

Altmüller T. 2007. Driver monitoring and drowsiness detection by steering signal analysis. PhD thesis, Universitat der Bundeswehr Munchen, Germany.

Krauchi K. 2007. The human sleep-wake cycle reconsidered from a thermoregulatory point of view. Physiology & Behavior 90(2-3): 236-245.

Krauchi K. and de Boer 2010. The interrelationship between sleep regulation and thermoregulation. Frontiers in Bioscience 15: 604-625.

Mount L. E. 1979. Adaptation to thermal environment. Man and his productive animals. Edward Arnold, London.

Philip P. and Sagaspe P. 2011. Sleep and accidents. Bulletin de l'Academie nationale de Medicine 195(7): 1635-1643.

The invention claimed is:

1. A method for detection of drowsiness of a person having a heart rate and a distal temperature, based on a relationship between the distal temperature and the heart rate, comprising:
   measuring and monitoring the distal temperature as a function of time using a temperature sensor, and
   measuring and monitoring the heart rate as a function of time, using a heart rate sensor,
   evaluating a change in balance between body heat loss and body heat production by comparing a rate of change of the distal temperature with a first threshold and, after passing said first threshold, comparing a rate of change of the heart rate with a second threshold using a computing unit that is programmed to compare the rate of change of the distal temperature with the first threshold and, after passing said first threshold, compare the rate of change of the heart rate with the second threshold, and that processes in real-time measured signals from the temperature sensor and the heart rate sensor,
   generating a drowsiness signal and alerting the person that onset of drowsiness is concluded when the computing unit detects that the rate of change of distal temperature passes said first threshold and, subsequently, the rate of change of heart rate passes said second threshold,
   wherein the drowsiness signal comprises an activating signal that prevents and/or delays drowsiness, and wherein the step of generating the drowsiness signal comprises initiating the activating signal that prevents and/or delays drowsiness.

2. The method according to claim 1, wherein the distal temperature is monitored by monitoring averaged values of the measured distal temperature and/or wherein the heart rate is monitored by monitoring averaged values of the measured heart rate, wherein the averaged values are a moving average and/or a progressing overall mean.

3. The method according to claim 2, wherein the distal temperature and the heart rate are monitored and compared by:
   calculating a progressing overall mean distal temperature from the measured distal temperature,
   calculating a progressing overall mean heart rate from the measured heart rate,
   monitoring the rate of change of the progressing overall mean distal temperature and comparing the rate of change of distal temperature by comparing the rate of change of the progressing overall mean distal temperature with the first threshold,
   after passing said first threshold, monitoring the rate of change of the progressing overall mean heart rate,
   comparing the rate of change of heart rate by comparing the rate of change of the progressing overall mean heart rate with the second threshold, and
   concluding that drowsiness may occur in the immediate future when the rate of change of progressing overall mean distal temperature passes said first threshold and, subsequently, the rate of change of the progressing overall mean heart rate passes said second threshold.

4. A device for detection of drowsiness of a person having a heart rate and a distal temperature, based on a relationship between the distal temperature and the heart rate, comprising:
   a temperature sensor for measuring the distal temperature as a function of time and
   a heart rate sensor for measuring the heart rate as a function of time,
   a computing unit for monitoring and comparing the measured distal temperature and the measured heart rate, and
   wherein the computing unit is programmed to compare a rate of change of the distal temperature with a first threshold and, after detecting the passing of said first threshold, to compare a rate of change of heart rate with a second threshold, and to cause a drowsiness signal to be generated and to cause the person to be alerted when the computing unit detects that the rate of change of distal temperature passes said first threshold and, subsequently, detects that the rate of change of the heart rate passes said second threshold,
   wherein the drowsiness signal comprises an activating signal that prevents and/or delays drowsiness, and wherein generating the drowsiness signal comprises initiating the activating signal that prevents and/or delays drowsiness.

5. The device according to claim 4, wherein the computing unit is programmed to monitor the distal temperature and/or the heart rate, by monitoring averaged values of the measured distal temperature and/or the measured heart rate, wherein the averaged values are a moving average and/or a progressing overall mean.

6. The device according to claim 5, wherein the computing unit is programmed to calculate the progressing overall mean distal temperature from the measured distal temperature and calculates the progressing overall mean heart rate from the measured heart rate,
   wherein the computing unit is programmed to monitor the distal temperature by monitoring the progressing overall mean distal temperature and to compare the rate of change of the progressing overall mean distal temperature with the first threshold, and further, after the computing unit detects the passing of said first threshold, to monitor the heart rate by monitoring the progressing overall mean heart rate and to compare the rate of change of the progressing overall mean heart rate with the second threshold, and to cause the drowsiness signal to be generated when the computing unit detects that the rate of change of the progressing overall mean distal temperature passes said first threshold and, subsequently, the rate of change of the progressing overall mean heart rate passes said second threshold.

* * * * *